United States Patent [19]

Sakai et al.

[11] 4,097,541

[45] Jun. 27, 1978

[54] PROCESS OF PRODUCING MAINLY MONOCYCLIC AROMATIC COMPOUNDS FROM UNUTILIZED CARBON RESOURCES MAINLY COMPOSED OF POLYCYCLIC AROMATIC COMPOUNDS

[75] Inventors: Tomoya Sakai, Nagoya; Naoki Negishi, Tokyo, both of Japan

[73] Assignee: Kogyo Kaihatsu Kenkyusho (Industrial Research Institut), Tokyo, Japan

[21] Appl. No.: 714,006

[22] Filed: Aug. 13, 1976

Related U.S. Application Data

[63] Continuation of Ser. No. 479,285, Jun. 14, 1974, abandoned.

[30] Foreign Application Priority Data

Jun. 21, 1973   Japan ................... 48-69221
Mar. 13, 1974   Japan ................... 49-28046
Mar. 14, 1974   Japan ................... 49-28541
Mar. 14, 1974   Japan ................... 49-28542

[51] Int. Cl.$^2$ ................... C07C 1/20; C07C 15/02
[52] U.S. Cl. ................... 260/668 R; 208/8; 208/107; 260/591; 260/667; 260/668 F
[58] Field of Search ................... 208/8, 44, 264, 107; 260/668 R, 667, 666 A, 666 PY, 591, 668 F

[56] References Cited

U.S. PATENT DOCUMENTS

| 1,430,585 | 10/1922 | Ramage | 260/668 R |
| 1,597,796 | 8/1926 | James | 208/8 |
| 1,949,891 | 3/1934 | Waterman | 208/8 |
| 1,960,977 | 6/1934 | Pier et al. | 260/667 |
| 2,106,973 | 2/1938 | Ellis | 208/8 |
| 2,766,306 | 10/1956 | Heinemann et al. | 260/667 |
| 2,990,364 | 6/1961 | Fowle et al. | 260/667 |
| 3,030,297 | 4/1962 | Schroeder | 208/8 |
| 3,197,518 | 7/1965 | Chapman et al. | 260/668 F |
| 3,210,432 | 10/1965 | Richter | 260/668 R |

FOREIGN PATENT DOCUMENTS

| 1,270,703 | 7/1960 | France | 260/668 F |
| 1,392,912 | 4/1964 | France | 208/107 |
| 348,252 | 5/1931 | United Kingdom | 208/107 |
| 273,493 | 7/1927 | United Kingdom | 260/667 |
| 397,901 | 8/1933 | United Kingdom | 260/667 |
| 403,708 | 12/1933 | United Kingdom | 260/667 |
| 435,192 | 9/1935 | United Kingdom | 260/667 |

Primary Examiner—C. Davis
Attorney, Agent, or Firm—Burgess, Ryan and Wayne

[57] ABSTRACT

A novel hydrocarbonylation, i.e., decarbonylation in the presence of hydrogen, is disclosed. By applying hydrodecarbonylation to a series of reactions, monocyclic aromatic hydrocarbons such as benzene can be obtained in high yield from polycyclic aromatic hydrocarbons or heavy oils containing such materials. Thus, the present invention provides a method of effective utilization of carbon sources.

10 Claims, 3 Drawing Figures

PROCESS OF PRODUCING MAINLY MONOCYCLIC AROMATIC COMPOUNDS FROM UNUTILIZED CARBON RESOURCES MAINLY COMPOSED OF POLYCYCLIC AROMATIC COMPOUNDS

This is a continuation, of application Ser. No. 479,285, filed June 14, 1974 and now abandoned.

BACKGROUND OF THE INVENTION

1. Field of the Invention

This invention is directed to a novel hydrodecarbonylation and more specifically, to a method of effective utilization of carbon sources in which monocyclic aromatic hydrocarbons such as benzene can be obtained in high yield from polycyclic aromatic hydrocarbons or heavy oils containing such materials.

2. Description of the Prior Art

A large amount of polycyclic aromatic hydrocarbons is present in heavy oil or residual oil obtained by cracking which is obtained during the ratification of petroleum. These hydrocarbons include compounds such as anthracene, phenanthrene, naphthacene, chrysene or the like. In order to effectively utilize these carbon resources, it has been attempted to degrade these polycyclic aromatic hydrocarbons by means of catalytic hydrogenation.

According to ordinary catalytic hydrogenation of heavy oil under high pressure using catalysts such as Fe, Ni, Co, Mo or the like, polycyclic aromatic hydrocarbons are decomposed only at the side chain but the poly rings thereof remain as they are. When catalytic hydrocracking is further continued, the polycyclic aromatic hydrocarbons are finally hydrogenated until alicyclic hydrocarbons such as cyclohexane and lower aliphatic hydrocarbons such as methane, ethane and the like are formed. However, useful monocyclic aromatic hydrocarbons such as benzene are not appreciably formed in conventional catalytic hydrogenation processes. For instance, see W. H. Wieser, et al. *Industrial and Engineering Chemistry*, Prod. Res. & Develop., 9, 350(1970); Cai von Rumohr, et al. Erdol u. Kohle, Erdgas, Petrochemie vereinigt mit Brennstoff Chemie, 25, 309(1972). In addition, there are many troubles resulting from carbonaceous byproducts formed during various reactions. Such a situation appears likewise in the case of liquefying coal in accordance with a Bergius' method using an iron catalyst, whereby the reaction stops mainly at the stage where a reaction product mixture of naphthalene, benzene and the like is formed, wherein benzene homogues exist only below ca. 10%.

Referring now to phenanthrene as a model compound, a conventional catalytic hydrogenation process generally proceeds to finally obtain alicyclic hydrocarbons such as cyclohexane and lower aliphatic hydrocarbons such as methane or ethane, as main products, but to obtain monocyclic aromatic hydrocarbones represented by benzene in low yield. These reactions of a series of catalytic hydrogenation are typically shown in the following reaction schemes:

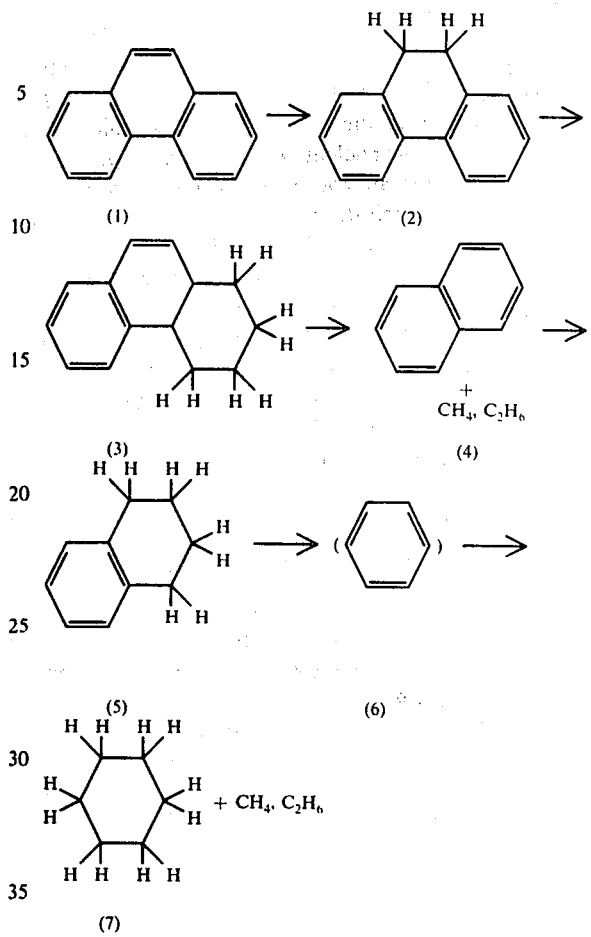

As is seen from the reaction schemes described above, phenanthrene (1) is partly hydrogenated to give 9,10-dihydrophenanthrene. When the dihydrophenanthrene is subjected to further hydrogenation, it is rearranged to obtain 1,2,3,4-tetrahydrophenanthrene (3). Further catalytic hydrogenation gives naphthalene (4) and lower aliphatic hydrocarbons, e.g., methane, ethane and the like and naphthalene (4) is further decomposed to give tetralin (5). Tetralin (5) is immediately dehydrogenated to obtain cyclohexane (7) and methane, ethane and the like via benzene (6) in situ.

In the course of investigations into the mechanism of hydrocracking of polycyclic aromatic hydrocarbons, we have found that one of the constituent reactions for degradation in accordance with the present invention is a novel reaction which is unknown in the literature. It was surprising that when an oxidation product of, e.g., residual oil obtained by cracking was subjected to the reaction of the present invention, the starting black residual oil was converted to monocyclic aromatics in considerably high yield. This means that polycyclic aromatic hydrocarbons contained in the residual oil were substantially converted into monocyclic aromatic hydrocarbons such as benzene. Since the novel reaction is hydrocracking in the absence of any catalyst for catalytic hydrogenation, we have named it "hydrodecarbonylation". The term "hydrodecarbonylation" herein means decarbonylation in the presence of hydrogen in which a stoicheometrical split-off of carbon monoxide is always effected.

Such hydrodecarbonylation does not occur in the presence of a catalyst for catalytic hydrogenation. When phenanthrenequinone is referred to as a model compound, in the case of a nickel catalyst, the hydrogenation proceeds at the oxygen atoms as well as the carbon atoms in the nucleus of the benzene rings to give alicyclic alcohols and/or octahydrophenanthrene. In the case of a Pt catalyst, the hydrogenation proceeds at 25° C to produce selectively perhydrophenanthrenediols. By the use of a Co-Mo-Al$_2$O$_3$ catalyst, phenanthrenequinone yields phenanthrene and water at high temperatures of 350° to 450° C under high pressures of 50 to 100 kg/cm$^2$ in the initial stage, which is followed by hydrocracking of phenanthrene to give naphthalene and lower hydrocarbons. In any case of conventional catalytic hydrogenation, it is extremely difficult to obtain useful monocyclic aromatic hydrocarbons from polycyclic aromatic hydrocarbons in high yield.

SUMMARY OF THE INVENTION

It is an object of the present invention to provide a novel reaction which can be utilized to obtain useful monocyclic aromatic hydrocarbons from polycyclic aromatic hydrocarbons in high yield.

It is a further object of the present invention to provide a method of effectively utilizing carbon sources contained in waste residual oil from purification steps of heavy oil, by applying a novel reaction which we have found.

Other objects of the present invention will appear herein.

DETAILED DESCRIPTION OF THE INVENTION

Figure 1:
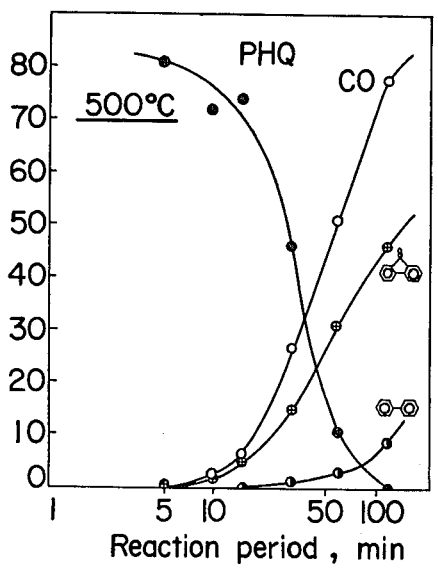
FIGS. 1(a) and (b) show a relative relationship between the distribution of products and time at reaction temperature of about 500° and 600° C respectively, when phenanthrenequinone is used as a starting material.
Figure 1:
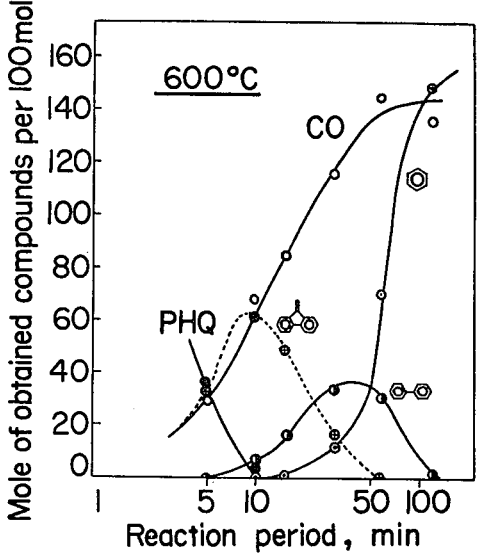
Figure 2:
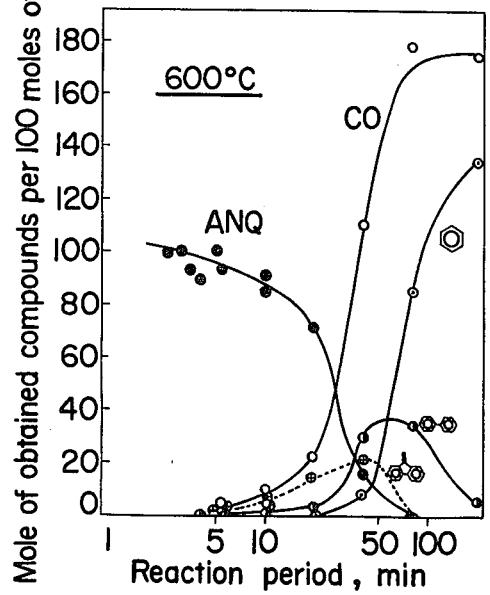
FIG. 2 shows a relative relationship between the distribution of products and time when anthraquinone is used.

The term "polycyclic aromatic hydrocarbon" hereinbelow includes aromatic hydrocarbons having at least one fused benzene system, which may be unsubstituted or substituted.

As is described above, hydrodecarbonylation of oxidation products of polycyclic aromatic hydrocarbons is necessarily accompanied by a stoichiometrical split-off of carbon monoxide. Explaining this with reference to phenanthrenequinone (1) as a model compound, when (1) is subjected to non-catalytic hydrocracking in the absence of any catalyst for catalytic hydrogenation as is shown in the reaction scheme — 1 below, fluorenone (2) and/or biphenyl (3) is obtained almost quantitatively depending upon reaction conditions and in any case, the amount of carbon monoxide (CO) by-produced is stoichiometric.

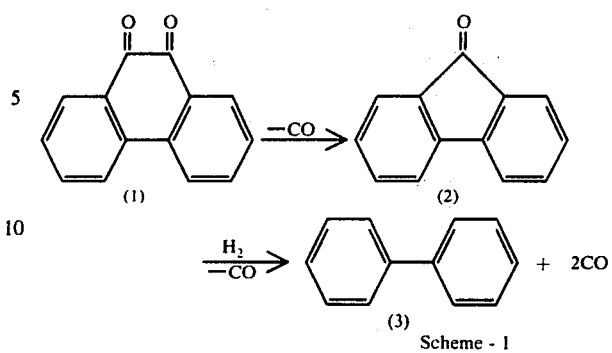

Scheme - 1

A definite mechanism is not clear but it is highly probable from the kinetics that an activated complex for the reaction scheme — 1 is higher in its energy than those for catalytic hydrocracking. Moreover, since an electron density can be concentrated at the 9,10-position and, in addition, a shift of electrons into a catalyst cannot take place in non-catalytic hydrocracking, it is assumed that decarbonylation proceeds easily in the reaction according to the present invention.

In order to examine the reaction scheme-1 above microscopically, the carbon atoms around the quinone moiety are numbered (1), (2), (3) and (4) as in (1), in which the oxygen atoms (O$_1$ and O$_2$) are bonded with the carbon atoms (3) and (4), respectively.

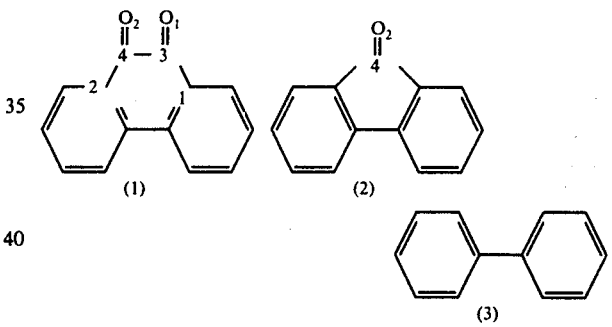

In the case where phenanthrenequinone (1) is subjected to non-catalytic hydrogenation in the absence of any catalyst, the oxygen O$_1$ and the carbon (3) and also the oxygen O$_2$ and carbon (4) respectively are split off as CO, whereby when the hydrogen atom is bonded with the carbon (1) and carbon (2) of the hydrocarbon residue, biphenyl (3) is formed, and instead of introducing of two hydrogen atoms, when the carbon (1) and carbon (4) are directly bonded, fluorenone (2) is formed. Fluorenone (2) is easily subjected to further hydrodecarbonylation to form biphenyl (3).

The starting materials which can be employed in accordance with the present invention are the oxidation products of condensed polycyclic aromatic hydrocarbons having at least one enone and/or enol bond in the ring(s) thereof or the corresponding dibasic acids, or mixtures thereof. Typical examples of starting materials are quinone type compounds, semiquinone type compounds, hydroquinone type compounds or the corresponding dibasic carboxylic acid type compounds. As long as polycyclic aromatic hydrocarbons are condensed and possess the molecular structure as is defined above, any polycyclic aromatic hydrocarbons can be the raw materials of the present invention. Inter alia, cata-condensed i.e., poly-condensed ring aromatics, e.g. polycyclic aromatic hydrocarbons are most preferred. Specific starting materials are exemplified by naphthoquinones, naphthalenesemiquinones, naphthalenehydroquinones, indenone, phenanthrenequinones, phenanthrenesemiquinones, phenanthrenehydroquinones, anthraquinones, anthracenesemiquinones, anthracenehydroquinones, fluorenone, etc., the corresponding dicarboxylic acids thereof, similar derivatives of pyrene or chrysene, and compounds having the following formulae:

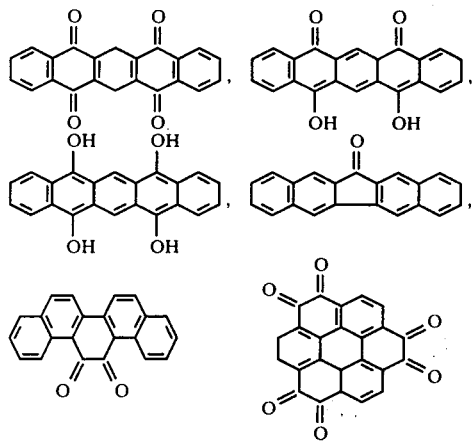

These starting compounds may be combined with other three to ten aromatic hydrocarbon residues via lower alkylene groups such as methylene or ethylene to form a more enormous polycyclic system. For example, the compound having the structure below can be used as a starting material in the present invention.

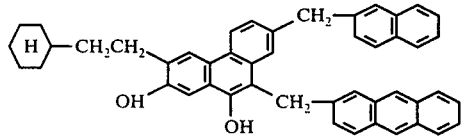

Further, these starting materials can also contain a thiophene type sulfur atom in their molecules. In this case, hydrodecarboxylation simultaneously accompanies the desulfurization.

These starting compounds can also be substituted with alkyl groups having 1 to 2 carbon atoms (e.g., methyl or ethyl), alkenyl groups having 2 to 3 carbon atoms (e.g., vinyl or allyl) or aryl groups (e.g., phenyl). The number of substituents are generally 1 or 2.

The starting materials can be obtained by conventional oxidation of polycyclic aromatic hydrocarbons in the presence of catalysts such as $V_2O_5$, $Fe_2O_2$ or CuO, or in the absence of any catalyst, the details of which are described in, e.g., R. Wandland, et al. Org. Syn.IV, 757(1963), Andreikor, E. I., Rusyanova, N. D. Khim Prod. Koksovaniya, Vglei Vostaka SSSR, No. 6, 141–8(1970); Fadeeva N. N., Proskurgakov, V. A., Chistyakov, A. N.; Zr.Prikl. Khim (Leningrad) 44, 2060–6(1971); Hasebe, K. Ueno, S., Wakabayashi, S., Yoshida, T.; Aromatikkusu, 23, 605–9(1971).

Polycyclic aromatic hydrocarbons to be oxidized can be found in topped crude oil, asphalt, cracked residues, coal tar, brown coal, etc. although the structures of polycyclic aromatic hydrocarbons contained in these natural residual oils are not necessarily identified, it is known that these natural residual oils are oxidized according to conventional oxidation methods. The $>C=O$ group appears in their molecules. For example, see L. Lenart, et al., Erdöl u. Kohle, Erdgas, Petrochemie vereinigt mit Brennstoff-Chemie, 25, 61(1972); P. G. Campbell, et al. Industrial and Engineering Chemistry, Prod. Res. & Develop., 3, 319(1966); J. Knotnenus, J. Inst. Petrol., 42, 355(1956); W. F. Oreshko, Izvest. Akad. Nauk, S.S.S.R., 1947, 249, 748 1642(C.A., 44, 2200, 2201(1950), 45, 2174(1951) ).

To illustrate successive reactions containing hydrodecarbonylation in accordance with the present invention, representative reaction maps with regard to some representative compounds are shown below:

(1) Naphthoquinone type compounds

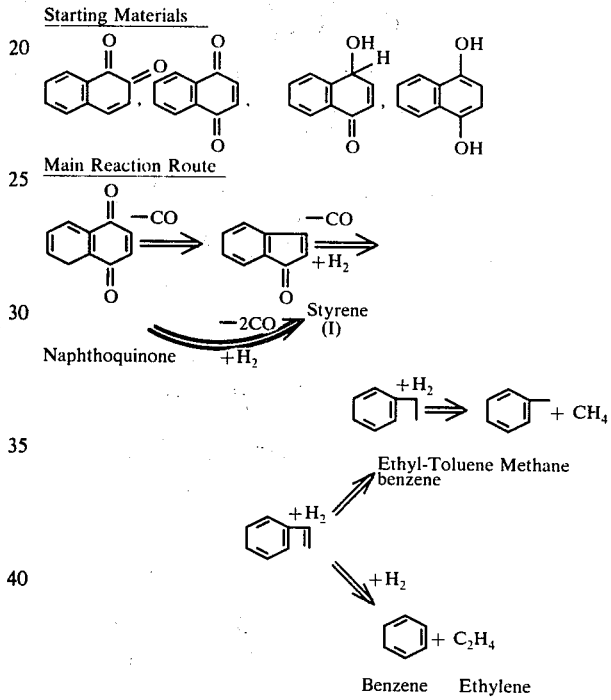

According to the reaction described above, 2 mols of CO are split off to 1 mol of naphthoquinone. The CO split off is stoichiometric. Since these reactions are successive ones, the actual products are not single products. The relationship between the starting material and reaction products can, however, be proved by the characteristics of the novel reaction described above, i.e., by accompanying the stoichiometric split-off of CO in any case where the products are either unitary or plural. As is seen from the examples hereinbelow, the formation of 1 mol of indenone is accompanied by the split-off of 1 mol of CO, and the formation of 1 mol of styrene is accompanied by the split-off of 2 mols of CO. A found value of the amount of the CO split off to a theoretical amount of the CO split off shows 98 to 106%, which well establishes the characteristic of the novel reaction of the present invention, where CO is almost stoichiometrically split off.

If desired, the thus obtained styrene can be successively subjected to non-catalytic hydrogenation to obtain ethylbenzene, toluene or benzene, as is shown in the reaction scheme above.

(2) Phenanthrenequinone type compounds and anthraquinone type compounds
Starting Materials
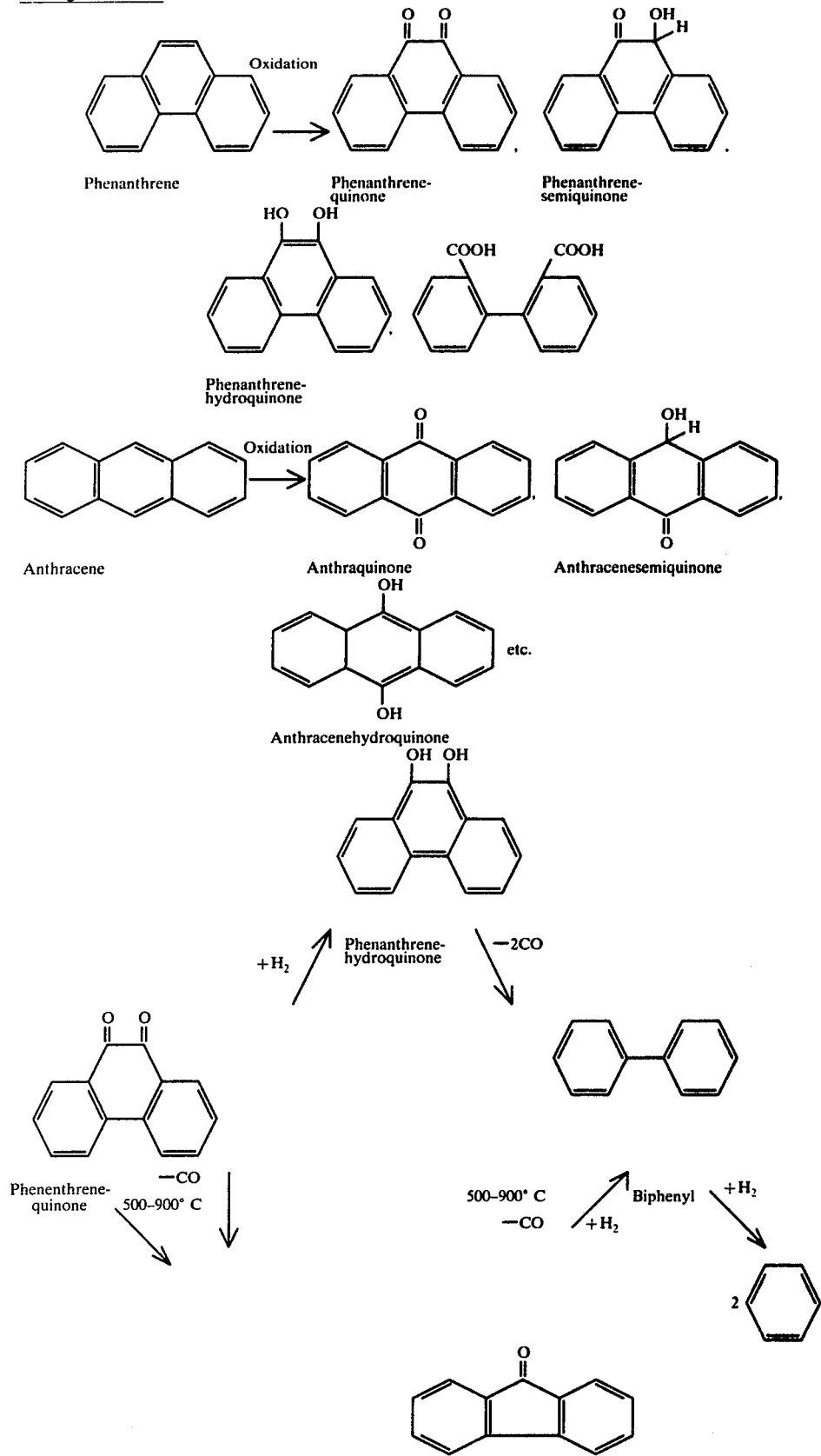

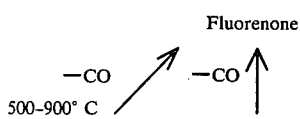

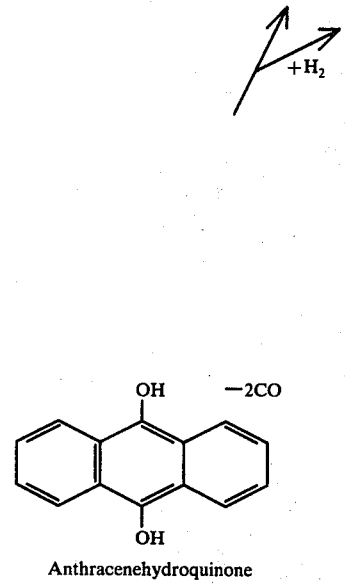

Upon the formation of benzene and biphenyl, this is accompanied by the necessary stoichiometric split-off of CO. Even if the reaction stops anywhere, a found value of the CO split off to a theoretical value of the CO measured from the distribution of the products is in a range of from 85 to 132% according to the examples, almost in a range of from 90 to 120%, which substantiates this novel reaction. The unreacted materials and the like contain the unreacted phenanthrenequinone and anthracenequinone. Phenanthrene, fluorene and anthracene are also formed during the course of the reactions in small amounts. However, these polycyclic aromatic hydrocarbons can be recycled as a raw material in the oxidation step. The unreacted starting materials of the present invention can also be recycled in the hydrodecarbonylation step. Accordingly, the loss of carbon is extremely slight.

It has already been described that this stoichiometric split-off of the carbon monoxide is of extreme importance in the present invention. Hydrodecarbonylation of the present invention generally proceeds by treating the system at temperatures of from about 500° to about 900° C in the absence of any catalyst while introducing hydrogen. However, since the kind of starting materials can widely vary as long as they meet the requirement described hereinabove, heating temperatures are not limitative, and accordingly, a preferred range of heating temperatures can vary depending upon as to what starting materials are contemplated to use. For instance, in case of using anthraquinone as a starting material, heating temperatures are preferably at about 600° C. In case of using phenanthrenequinone, preferred temperatures are ordinarily at about 500° C. Of course, the heating temperature also varies depending upon the residence time. If a residence time can be relatively prolonged, relatively low heating temperatures are sufficient for the reaction of the present invention.

To illustrate the relative non-criticality of the reaction conditions, runs of various conditions are shown in the examples, the results of which are recorded on a graph paper with the mole distribution of products on the vertical axis and time(min.) by a logarithmic scale horizontally. As is clearly seen from the figures, reaction conditions which give desired products can easily be fixed.

Hydrodecarbonylation in accordance with the present invention is generally conducted under atmospheric pressure.

The effects of the present invention are listed below:

(1) Monocyclic hydrocarbons such as benzene, toluene, xylene, styrene and the like which have high utility value are obtained in high yield by utilizing novel hydrodecarbonylation;

(2) Heavy oil which has had less utility value heretofore can be effectively utilized as carbon resources;

(3) No catalyst is needed in the present invention so that no operations such as recovery of a catalyst, etc. are required. Accordingly, low cost can be realized and at the same time, industrial pollution due to catalyst treatment would not occur;

(4) The reactions proceed under atmospheric pressure;

(5) The hydrogen to be consumed is small as compared with catalytic hydrocracking. Accordingly, the waste of hydrogen can be prevented;

(6) Since it is possible to keep the reaction conditions under high pressure low temperature condition and there is also present the possibility of the reactions in liquid phase, it would be possible to utilize apparatuses for conventional processes.

The present invention will be explained with reference to the examples below but is not limited thereto.

EXAMPLES 1 - 11

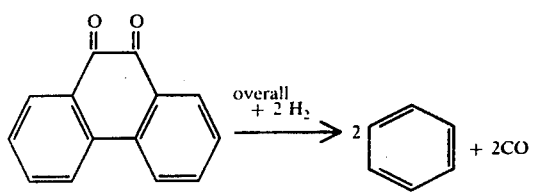

Into a transparent quartz ampoule reactor having an inner volume of 40 ml, whose inside was previously rendered in vacuous, phenanthrenequinone was first charged and hydrogen was then introduced thereinto at about 25° C until the pressure reached ca. 400 mmHg. The ampoule was then sealed and placed in a stainless steel furnace having 6 holes of a 3 cm diameter. The system was heated at temperatures of from about 400° C to about 650° C while varying the reaction time. The reaction was carried out for a certain period of time. Thereafter, the system was quenched in water. The results are shown in the table below, in which conversion rate and CO balance are expressed by the following equations, throughout the examples:

$$\text{Conversion rate}(\%) = \frac{(\text{Starting material}) - (\text{Remaining starting material})}{\text{Starting material}} \times 100$$

CO balance estimated from the reaction products(%) =

$$\frac{\text{Amount of CO formed per 1 mol of starting material}}{\text{Calculated amount of CO per 1 mol of starting material}} \times 100$$

Table 1

| Example No. | Phenanthrenequinone | | | | | | | | | | |
|---|---|---|---|---|---|---|---|---|---|---|---|
| | 1 | 2 | 3 | 4 | 5 | 6 | 7 | 8 | 9 | 10 | 11 |
| Reaction Temperature (° C) | 482 | 485 | 488 | 496 | 502 | 568 | 580 | 599 | 601 | 618 | 640 |
| Reaction Time (min.) | 10 | 13 | 30 | 60 | 120 | 5 | 10 | 155 | 30 | 60 | 120 |
| $H_2$/Phenanthrenequinone *1 | 14.4 | 14.9 | 15.6 | 15.7 | 14.9 | 11.7 | 12.7 | 12.0 | 11.7 | 13.2 | 13.1 |
| Conversion Rate (%) | 28.1 | 26.1 | 52.9 | 89.5 | 100 | 64.6 | 100 | 100 | 100 | 100 | 100 |
| Distribution of Products *2 | | | | | | | | | | | |
| CO | 2.5 | 6.4 | 26.7 | 51.0 | 77.7 | 29.8 | 67.5 | 85.1 | 116.0 | 144.8 | 135.8 |
| Benzene | 0.0 | 0.0 | 0.0 | 0.0 | + *3 | 0.0 | 0.1 | 0.9 | 11.5 | 69.6 | 148.1 |
| Biphenyl | 0.0 | + | 0.9 | 2.7 | 8.9 | + | 6.3 | 16.3 | 33.3 | 29.9 | 1.8 |
| Fluorene | 0.5 | 0.5 | 3.9 | 6.3 | 8.3 | 0.8 | 2.8 | 2.8 | 3.9 | 5.2 | 4.5 |
| Fluorenone | 2.4 | 5.0 | 14.6 | 31.1 | 46.2 | 32.5 | 61.3 | 49.1 | 16.4 | + | 0.0 |
| Phenanthrene | 0.0 | 0.0 | 0.0 | 0.0 | 0.0 | 0.0 | 0.0 | + | 0.5 | 3.0 | 3.1 |
| Unreacted phenanthrenequinone | 71.9 | 73.9 | 47.1 | 10.5 | + | 35.4 | + | 0.0 | 0.0 | 0.0 | 0.0 |
| CO Balance (%) | 86.2 | 116.4 | 131.5 | 119.2 | 108.1 | 89.0 | 87.9 | 99.6 | 117.9 | 107.6 | 86.9 |

*1 Molar ratio;
*2 Mol number to 100 mols of starting material;
*3 Trace

As is clearly seen from the results above, CO balance of the reaction system ranges from 92 to 124%, which is substantially in stoichiometrical relation since the deviation is considered to be within limit of the experimental variation. In other words, noncatalytic hydrodecarbonylation proceeds almost stoichiometrically. Thus, phenanthrenquinone was easily degraded into lower hydrocarbons such as benzene and biphenyl in high yield.

EXAMPLES 12 - 17

Anthraquinone was treated in a similar manner to Example 1. The results are shown in table 2 below.

EXAMPLES 18 - 23

1,4-Naphthoquinone was similarly treated to Example 1. The results are shown in table 3 below.

Table 2

| | Anthraquinone | | | | | |
|---|---|---|---|---|---|---|
| Example No. | 12 | 13 | 14 | 15 | 16 | 17 |
| Reaction Temperature (° C) | 575 | 590 | 595 | 610 | 620 | 630 |
| Reaction Time (min.) | 5.0 | 10.0 | 20.0 | 40.0 | 80.0 | 160.0 |
| $H_2$/Anthraquinone *1 | 10.6 | 10.5 | 11.3 | 11.7 | 12.4 | 12.2 |
| Conversion Rate (%) | 0.0 | 9.3 | 28.7 | 84.0 | 100 | 100 |
| Distribution of Products *2 | | | | | | |
| CO | + | 3.8 | 22.0 | 110.5 | 178.5 | 176.4 |
| Benzene | 0.0 | 0.0 | + | 8.1 | 84.8 | 133.6 |
| Biphenyl | + | + | 3.2 | 29.9 | 34.3 | 4.6 |
| Fluorene | 0.0 | + | + | 3.0 | 5.6 | 5.4 |
| Fluorenone | 0.8 | 4.1 | 14.9 | 21.4 | + | + |
| Anthracene | + | + | . | 0.9 | 1.8 | 1.6 |
| Unreacted Anthraquinone | 100.1 | 90.7 | 71.3 | 16.0 | 0.0 | 0.0 |
| Others | 0.0 | 0.2 | 0.3 | 0.5 | 2.0 | 2.0 |
| CO Balance (%) | 0.0 | 92.7 | 103.3 | 119.5 | 112.2 | 119.0 |

*1 Molar ratio
*2 Mol number to 100 mols of starting material

Table 3

| | 1,4-Naphthoquinone | | | | | |
|---|---|---|---|---|---|---|
| Example No. | 18 | 19 | 20 | 21 | 22 | 23 |
| Reaction Temperature (° C) | 560 | 580 | 580 | 580 | 585 | 595 |
| Reaction Time (min.) | 5.0 | 10.0 | 12.0 | 15.0 | 20.0 | 40.0 |
| $H_2$/Naphthoquinone *1 | 10.2 | 19.9 | 10.8 | 10.0 | 10.4 | 10.0 |
| Conversion Rate (%) | 27.1 | 90.2 | 96.3 | 98.6 | 100 | 100 |
| Distribution of Products *2 | | | | | | |
| CO | 13.3 | 52.7 | 101.6 | 108.6 | 123.8 | 140.8 |
| Methane | + | 1.7 | 5.3 | 8.5 | 14.8 | 30.8 |
| Ethane | 0.0 | 0.0 | 0.5 | 1.8 | 4.6 | 10.8 |
| Ethylene | 1.5 | 4.2 | 7.6 | 7.7 | 8.2 | 8.4 |
| Benzene | 1.5 | 4.7 | 10.3 | 12.7 | 17.4 | 30.4 |
| Toluene | 0.1 | 0.3 | 1.0 | 2.1 | 5.7 | 8.3 |
| Ethylbenzene | + | 3.1 | 7.3 | 9.7 | 12.2 | 2.6 |
| Styrene *3 | 4.8 | 16.4 | 26.6 | 26.7 | 20.1 | 15.9 |
| Indene | 0.0 | 0.5 | 0.8 | 0.7 | 1.0 | 1.1 |
| Unidentified Materials | 0.0 | 0.5 | 1.0 | 1.6 | 2.4 | 1.9 |
| Naphthalene | 0.0 | 0.5 | 0.7 | 0.9 | 1.2 | 3.0 |
| Unreacted 1,4-naphthoquinone | 72.9 | 9.8 | 3.7 | 1.4 | 0.0 | 0.0 |
| Others *4 | 0.1 | 1.3 | 1.2 | 1.5 | 2.2 | 2.3 |

Table 3-continued

| | 1,4-Naphthoquinone | | | | | |
|---|---|---|---|---|---|---|
| Example No. | 18 | 19 | 20 | 21 | 22 | 23 |
| CO Balance (%) | 103 | 106 | 106 | 99 | 105 | 111 |

*1 Molar ratio;
*2 Mol number to 100 mols of starting material;
*3 Polymerization occurred partly.
*4 Carbonaceous materials were present.

EXAMPLE 24

Phenanthrenequinone was treated in a similar manner to the procedure of Example 1 but the procedures were continuously conducted at temperature of 800° C using a flow-type apparatus. The results were substantially the same as in Example 1.

EXAMPLE 25

Into an SUS 32-made autoclave having an inner diameter of 50 mm and a length of 200 mm, there was charged as a starting material a fraction containing naphthalene or more polycyclic aromatic hydrocarbons, of the residual oil which was obtained from a naphtha steam cracker for the preparation of ethylene. Air was bubbled thereinto in a weight ratio of 1 per an hour to 1 of the starting material for 1.2 hours, whereby the temperature of the system was 150° C. After purging with nitrogen, hydrogen at 10 atm pressure was bubbled through the system for 0.3 hours at 550° C in such an amount that the bubbling condition becomes similar. The total yield of benzene, toluene and xylene reached 30% based on the starting material. No sulpher was found in the remained oil.

The oil remaining in the autoclave was again subjected to oxidation with air and hydrocracking as described above, the sum of the yield of benzene, toluene and xylene became 38% based on the starting material.

What is claimed is:

1. A method for decarbonylating an oxygen-containing condensed polycyclic aromatic hydrocarbon having at least one group selected from the group consisting of carbonyl, hydroxyl, and carboxyl which consists essentially of heating said oxygen-containing condensed polycyclic aromatic hydrocarbon at a temperature of from about 500° C to about 900° C under atmospheric pressure in contact with hydrogen and in the absence of a catalyst, to thereby stoichiometrically split off carbon monoxide.

2. A method according to claim 1, wherein said oxygen-containing condensed polycyclic aromatic hydrocarbon is prepared by oxidation of the corresponding condensed polycyclic aromatic hydrocarbon.

3. A method according to claim 2 wherein said oxygen-containing condensed polycyclic aromatic hydrocarbon is a member selected from a group consisting of naphthoquinone, naphthalenesemiquinone, naphthalenehydroquinone, indenone, anthraquinone, anthracenesemiquinone, anthracenehydroquinone, phenanthrenequinone, phenanthrenesemiquinone, phenanthrenehydroquinone, pyrenequinone, pyrenesemiquinone, pyrenehydroquinone, chrysequinone, chrysenesemiquinone, chrysenehydroquinone and a member selected from the group consisting of those represented by the formula

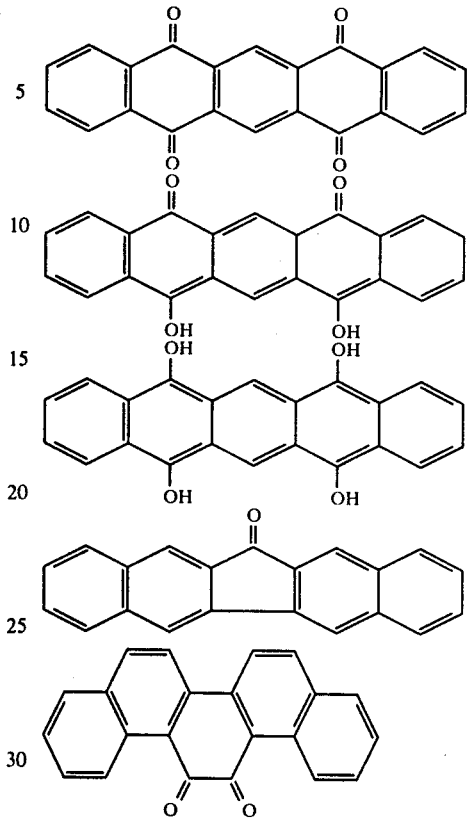

4. A method according to claim 1 wherein said condensed polycyclic aromatic hydrocarbon is a member selected from the group consisting of unsubstituted polycyclic aromatic hydrocarbons and substituted polycyclic aromatic hydrocarbons substituted by one or two alkyl groups having up to 2 carbon atoms, alkylene groups having up to 3 carbon atoms, and an aryl group having up to 6 carbon atoms.

5. A method according to claim 2 wherein said condensed polycyclic aromatic hydrocarbon is a member selected from the group consisting of topped crude oil, asphalt, cracked residue, coal tar and brown coal.

6. A method for decarbonylating phenanthrenequinone whch consists essentially of heating said phenanthrenequinone at a temperature of about 400° C to 650° C under atmospheric pressure in contact with hydrogen and in the absence of a catalyst, to thereby stoichiometrically split off carbon monoxide.

7. A method according to claim 4 wherein said oxygen-containing condensed polycyclic aromatic hydrocarbon is anthraquinone.

8. A method according to claim 4 wherein said oxygen-containing condensed polycyclic aromatic hydrocarbon is 1,4-naphthoquinone.

9. A method according to claim 2 wherein said condensed polycyclic aromatic hydrocarbon is a member selected from the group consisting of naphthalene, anthracene, phenanthrene, pyrene, chrysene and fluorene.

10. The process of claim 1 wherein the oxygen containing condensed polycyclic aromatic hydrocarbon is a composition selected from the group consisting of polycyclic aromatic hydrocarbons having at least one enone group in the rings, polycyclic aromatic hydrocarbons having at least one enol group in the rings and the corresponding dibasic acids and mixtures thereof.

* * * * *